United States Patent
Park et al.

(10) Patent No.: US 7,101,535 B2
(45) Date of Patent: Sep. 5, 2006

(54) ORAL COMPOSITIONS AGAINST HALITOSIS

(75) Inventors: Sang-Ki Park, Daejeon (KR);
Sang-Nyun Kim, Daejeon (KR);
Hyoung-Kook Park, Daejeon (KR);
Moon-Moo Kim, Daejeon (KR)

(73) Assignee: LG Household & Health Care Ltd., Seoul (KR)

( * ) Notice: Subject to any disclaimer, the term of this patent is extended or adjusted under 35 U.S.C. 154(b) by 310 days.

(21) Appl. No.: 10/250,631

(22) PCT Filed: Dec. 18, 2001

(86) PCT No.: PCT/KR01/02197

§ 371 (c)(1),
(2), (4) Date: Jun. 20, 2003

(87) PCT Pub. No.: WO02/49589

PCT Pub. Date: Jun. 27, 2002

(65) Prior Publication Data

US 2004/0224287 A1    Nov. 11, 2004

(30) Foreign Application Priority Data

Dec. 21, 2000    (KR)    .................... 2000-79562

(51) Int. Cl.
*A61K 8/97* (2006.01)
*A61K 36/00* (2006.01)
(52) U.S. Cl. .................. 424/58; 424/769; 424/773; 424/775; 514/901
(58) Field of Classification Search ............... None
See application file for complete search history.

(56) References Cited

U.S. PATENT DOCUMENTS 4,465,673 A * 8/1984 Tanaka et al. ............... 514/25
6,241,975 B1 * 6/2001 Moon et al. ................. 424/58

FOREIGN PATENT DOCUMENTS

| JP | 60-75418 | 4/1985 |
| JP | 63-264516 | * 11/1988 |
| KR | 91-18007 | 11/1991 |
| KR | 93-2725 | 4/1993 |
| KR | 97-8154 | 5/1997 |

OTHER PUBLICATIONS

Derwent Abstract 1989-091239, "Bad breath inhibitor" (1988).*
PCT International Search Report, Apr. 16, 2002, for Park, et al., PCT/KR01/02197, "Oral Composition Against Halitosis." [Exhibit 5].
PCT International Preliminary Examination Report, May 30, 2003 for Park, et al., PCT/KR01/02197 "Oral Compositions Against Halitosis." [Exhibit 6].

* cited by examiner

*Primary Examiner*—Frederick Krass
(74) *Attorney, Agent, or Firm*—Law Offices of Albert Wai-Kit Chan, LLC

(57) ABSTRACT

Disclosed is an oral composition effective against halitosis comprising an extract from Moutan (*Paeonia suffruticosa* Andrews) bark as an active ingredient, which is capable of inhibiting and eliminating substances causing oral malodor. The oral composition of the invention compromises an extract from Moutan bark, a medicinal herb, as an active ingredient, formulated in conjunction with to a conventional oral composition, thereby providing long lasting and powerful eliminating and preventive effects against halitosis.

4 Claims, No Drawings

ORAL COMPOSITIONS AGAINST HALITOSIS

This application is a 371 of PCT/KR01/02197, filed Dec. 18, 2001.

TECHNICAL FIELD

The present invention relates in general to an oral composition effective against halitosis, which is capable of inhibiting and eliminating substances causing oral malodor, and more particularly to an oral composition effective against halitosis comprising an extract from Moutan bark as an active ingredient.

BACKGROUND ART

In general, halitosis is caused by acquired systemic disease or substances inducing malodor, produced through degradative action of certain enzymes such as decarboxylase, or deaminase (L-cysteine desulfhydrase or L-methionine-ɣ-lyase) on amino acids resulting from the decomposition of salivary proteins, food particles, and the like by microorganisms in the oral cavity. Sulfide compounds, which are contained in ingested garlic or hot pepper, are also responsible for oral malodor. Main components causing halitosis comprise volatile sulfide compounds (hereinafter referred to as "VSC") including, for example, hydrogen sulfide ($H_2S$), methyl mercaptan ($CH_3SH$), dimethyl mercaptan (($CH_3)_2S$) and the like. Particularly, methylmercaptan is known as a main compound of offensive odor contributing to halitosis. Volatile amine compounds including trimethyl amine (($CH_3)_3N$) or δ-aminovaleric acid causing fishy stink resulting from staleness of fishes are also major compounds responsible for oral malodor. Other substances causing oral malodor include aldehydes, fatty acids, ammonia and pyridines.

In addition, methods of eliminating halitosis by removing such VSC are disclosed in prior patents including Korean Pat. Laid-open Publication No. 97-8154 and Japanese Pat. Laid-open Publication No. 60-75418.

DISCLOSURE OF THE INVENTION

The present inventors have conducted studies to find a material having a long lasting elimination effect against halitosis, and found that an extract from Moutan bark is an effective agent for removing VSC and is further capable of exhibiting a long lasting and powerful effect against halitosis. Thus, it is an object of the present invention to provide an oral composition comprising the extract from Moutan bark effective against halitosis.

BEST MODE FOR CARRYING OUT THE INVENTION

Moutan bark used in the invention is prepared from the root of a plant, Moran (also called Moutan; Family Paeoniaceae) with the scientific name *Paeonia suffruticosa* Andrews. Root of the plant is collected in autumn and only bark of the root is dried under sunlight. Chemical components of Moutan bark include paeonol and its glycosides, benzoates and campesterol. Moutan bark has been used as a tranquilizer, an antipyretic, an anti-inflammatory agent and the like in Oriental medicine, owing to its effects of reducing body temperature and promoting blood circulation. Its safety has already been assured, as Moutan bark has been used in Oriental medicine for a long time. Further, upon applying it topically, there is little irritation to the skin and mucosa, ensuring that it is a very safe plant.

An extract from Moutan bark was prepared as follows.

Moutan bark was ground to 10 to 200 in mesh size, added with an extraction solvent and cold-precipitated for 48 hours. The solution was filtered and concentrated to offer an extract of Moutan bark. The extraction solvent used is one or a combination of two or more selected from the group consisting of purified water, methanol, ethanol, propanol, butanol, ethyleneglycol, propyleneglycol, 1,3-butyleneglycol, ethylacetate and acetone. According to the invention, the oral composition comprises an extract from Moutan bark preferably in an amount of 0.01 to 2% by weight, relative to the total weight of the composition. When comprising an extract of less than 0.01% by weight, the composition is hardly capable of exhibiting an inhibitory effect against halitosis. When comprising 2% or more by weight, it is not expected that the inhibition effect becomes stronger according to the increase of the extract content, and further there is a problem in marketing an article due to unattractive coloration.

The oral composition according to the invention may be formulated in a form of toothpaste, mouthwash, spray or other agents for oral hygiene. Among these, toothpaste and mouthwash were embodied in experiments to test the invention. As a preparative example, toothpaste can be formulated using a common process known in the art, as follows.

The composition for toothpaste comprises an extract from Moutan bark as an active ingredient and may further contain oral disinfectant, abrasive, humectant, binder, frothing agent, sweetening agent, preservative, buffering agent and flavoring agent.

Oral disinfectant may be triclosan or cetylpyridium chloride and are employed alone or in combination thereof in an amount of 0.01 to 1% by weight.

As for an abrasive, calcium carbonate, calcium monohydrogen phosphate, precipitated silica, hydrous alumina, silica gel, insoluble sodium m-phosphate or zirconium silicate may be employed alone or in combination of two or more thereof. The abrasive of the invention is contained at an amount of 20 to 70% by weight, preferably 35 to 55% by weight.

As for a humectant, glycerine, sorbitol solution, amorphous sorbitol solution or polyethylene glycol may be employed alone or in combination of two or more thereof. The humectant used in the invention may be contained at an amount of 20 to 60% by weight, preferably 20 to 50% by weight.

With regard to a binder, in general, carrageenan, Xanthan gum, carboxylmethyl sodium cellulose, carboxyl vinylpolymer and sodium alginate are suitable for use in the invention. The binder in the invention may be contained at an amount of 0.1 to 3.0% by weight, preferably 0.5 to 2.0% by weight.

Available frothing agents include anionic surfactants such as lauryl sodium sulfate and sodium lauryl sarcosinate, and nonionic surfactants such as sorbitan fatty acid ester, polyoxyethylene hydrogenated castor oil and polyoxyethylene polyoxypropylene copolymer. The combination of an anionic surfactant and a nonionic surfactant or each alone may be contained at an amount of 0.5 to 5.0% by weight, preferably 0.5 to 2.5% by weight.

As for a sweetening agent, sodium saccharin, aspartame, acesulfame, stevioside or glycyrrhizinic acid may be employed alone or in combination of two or more. The sweetening agent in the invention is contained at an amount of preferably 0.05 to 0.5% by weight.

As for a preservative, paraoxy benzoate ester, benzoate or sodium benzoate may be employed alone or in combination of two or more thereof in an amount of preferably 0.05 to 0.25% by weight.

In addition, an anti-caries agent for use in the invention may be a fluoride compound, and an agent for preventing discoloration of the composition of the invention may be sodium m-bisulfite.

As for a buffering agent, phosphoric acid, sodium phosphate, citric acid, sodium citrate, succinic acid, sodium succinate, tartaric acid or sodium tartarate may be employed alone or in combination of two or more thereof in an amount of preferably 0.02 to 1.5% by weight.

Available flavoring agents include odoriferous substances and food flavoring agents, for example, peppermint oils, menthol, spearmint oils, carvon, anice oils, anitol, Eucalyptus oils, Clove oils, eugenol, Winter green oils, methyl salicylate, Cinnamon oils, cinnamic aldehyde and other aromatic components. The flavoring agent in the invention is contained alone or in combination of two or more of the above components at an amount of 0.1 to 2.0% by weight, preferably 0.5 to 1.5% by weight.

EXAMPLE 1

Preparation of Extracts From Moutan Bark 100 g dried Moutan bark was ground to 10 to 200 to in mesh size using a grinder, added with 500 ml of 80% (v/v) ethanol solution, cold-extracted for 48 hours at room temperature, and then filtered using a Whatman #2 paper. A filtered extract was concentrated under reduced pressure at 45° C., the concentrate thus obtained was employed as an extract for use in the invention.

EXPERIMENTAL EXAMPLE 1

Evaluation of Inhibitory Effects of an Extract From Moutan Bark on a Main Compound (methylmercaptan) Causing Halitosis Concentrations of methylmercaptan in the oral cavity were measured using a halimeter (Interscan co., USA) to determine inhibitory effects of the extract obtained in Example 1 on methylmercaptan, a main compound causing halitosis.

A standard solution of methylmercaptan (1 µg/µl in benzene) was diluted into 0.2 M potassium phosphate buffer (pH 7.5) and adjusted to a value ranging from 500 to 600 ppb as measured using a halimeter. The diluted solution was employed as a solution causing oral malodor in this experiment. An extract from Moutan bark was dissolved in 0.2 M potassium phosphate buffer (pH 7.5) to a 1% concentration of the extract. The 1% solution was employed as a halitosis inhibitor in this experiment. For a control group, 500 µl of the phosphate buffer and 500 µl of the solution causing oral malodor were combined in a test tube with a cap, and for an experimental group, 500 µl of the extract solution and 500 µl of the solution causing oral malodor were combined in a test tube with a cap. After each of the test tubes was let stand in a water bath at 36.5° C. for 5 min, the concentrations of sulfide compounds in the headspace were measured using a halimeter. Experiments for the control groups and the experimental groups were conducted in triplicate and in quadruplicate, respectively, and measurements were averaged.

Inhibition rate of the 1% extract solution obtained from Moutan bark on a substance causing oral malodor is represented in Table 1.

TABLE 1

Inhibition rates on methylmercaptan

| Extract | Inhibition rate (unit: %) |
|---|---|
| Control group | 0 |
| Experimental group | 81 |

As shown in Table 1, the extract from Moutan bark exhibited a significant halitosis inhibition effect by lowering the concentration of methylmercaptan.

EXAMPLE 2

Purification of an Extract From Moutan Bark Through Fractionation Employing Various Solvents 1 g of the extract from Moutan bark obtained in Example 1 was suspended in 100 ml of water and placed in a separatory funnel. The suspension was solvent fractionated twice with an equal volume of n-hexane and the solution was concentrated under reduced pressure to obtain 80 mg of n-hexane fraction. By the same method, dichloromethane, ethylacetate and n-butanol were employed sequentially to solvent-fractionate, producing fractions of 120 mg, 400 mg and 280 mg, respectively, and the final fraction was 120 mg of water fraction.

The ethylacetate fraction obtained above could be prepared by suspending an extract from Moutan bark in water, fractionating with ethyl ether, followed by extracting the remaining solution with ethylacetate. Alternatively, the fraction could be obtained either by extracting an extract from Moutan bark with n-hexane, followed by extracting the residual Moutan bark with ethylacetate, or by directly extracting Moutan bark with ethylacetate.

EXPERIMENTAL EXAMPLE 2

Evaluation of Inhibitory Effects of Various Solvent Fractions on a Main Compound Causing Halitosis Concentrations of methylmercaptan in the oral cavity were measured using a halimeter to determine inhibitory effects of the solvent fractions obtained in Example 1 against volatilization of methylmercaptan, a main compound causing halitosis. The similar method to the experimental example 1 was employed, except that the concentrations of the extracts and the solvent fractions were 0.5% each. The results are shown in the Table 2 below.

TABLE 2

Inhibition rates on methylmercaptan

| Fraction | Inhibition rate (unit: %) |
|---|---|
| Control group | 0 |
| Extract | 56 |
| n-hexane fraction | 11 |
| Dichloromethane fraction | 30 |
| Ethylacetate fraction | 73 |
| n-BuOH fraction | 44 |

As shown in Table 2, the inhibitory effect of an extract from Moutan bark against halitosis was strongest in the ethylacetate fraction with a 73% inhibition rate. Thus, it was found that a component of Moutan bark effective for inhibiting halitosis is present in the ethylacetate fraction.

EXAMPLE 3

Preparation of Mouthwashes Each Comprising an Extract From Moutan Bark

Respective ingredients typically used in a conventional mouthwash were employed as main components to prepare exemplary mouthwashes (Examples 3-1 to 3-3) and a conventional mouthwash (Comparative example 3-1) as listed in Table 3 below.

TABLE 3

Compositions of mouthwashes (unit: weight %)

| Component | Ingredient | Examples 3-1 | 3-2 | 3-3 | Comp. Ex. 3-1 |
|---|---|---|---|---|---|
| humectant | glycerine | 7.0 | 7.0 | 7.0 | 7.0 |
| anticavity agent | sodium fluoride | 0.02 | 0.02 | 0.02 | 0.02 |
| buffering agent | sodium citrate | 0.4 | 0.4 | 0.4 | 0.4 |
| buffering agent | citric acid | 0.005 | 0.005 | 0.005 | 0.005 |
| sweetening agent | sodium saccharin | 0.011 | 0.011 | 0.011 | 0.011 |
| emulsifier | F-127 | 1.0 | 1.0 | 1.0 | 1.0 |
|  | ethanol | 4.0 | 4.0 | 4.0 | 4.0 |
| disinfectant | cetylpyridium chloride | 0.005 | 0.005 | 0.005 | 0.005 |
| preservative | methylparaben | 0.1 | 0.1 | 0.1 | 0.1 |
| preservative | propylparaben | 0.05 | 0.05 | 0.05 | 0.05 |
| flavoring agent | combined flavorant | 0.12 | 0.12 | 0.12 | 0.12 |
| Active ingredient | extract | 0.01 | 0.5 | 2 | — |
|  | purified water | balance | balance | balance | balance |

EXPERIMENTAL EXAMPLE 3

Comparison of Inhibitory Effect of Exemplary Mouthwashes (Examples 3-1 to 3-3) With That of a Comparative Mouthwash (Comparative Example 3-1) Against Volatilization of Garlic Odor in a Clinical Oral Application Experiment A cross-over test was performed with 18 subjects, male or female, not having dental caries.

Commercial garlic powder which contains sulfide compounds was dispersed in water and left for 24 hours. The suspension was diluted to a solution with a value ranging from 350 to 450 ppb, as the concentration of sulfide compounds therein was measured using a halimeter. The diluted garlic solution was employed as a solution causing oral malodor in this experiment. For an experimental group, 500 µl of the exemplary mouthwashes (Examples 3-1 to 3-3) and 500 µl of the diluted garlic solution were mixed, and for a control group, the comparative mouthwash (Comp. Ex. 3-1) and the diluted garlic solution were mixed. The mixture was held in a subject's closed mouth while applied to the oral cavity using the tongue for 30 seconds, followed by a measurement using a halimeter; and 30 minutes later, a second measurement was performed to determine whether inhibitory effects of the mouthwashes on volatilization of garlic odor were sustained.

Measurement by means of a halimeter was performed in the following manner. Before measurement, a subject breathed only through the nose with a closed mouth for one minute. For measurement, the subject had a probe inserted about 1.5 cm into the mouth and held for about 15 seconds. At this time, the probe was not allowed to touch with the tongue. The subject kept his/or her lips open about 3 to 4 mm and kept breathing only through the nose.

The results are shown in Table 4 below.

TABLE 4

Levels of sulfide compounds of garlic (unit: ppb)

| Examples | Immediately after application | 30 min after application |
|---|---|---|
| Ex. | | |
| 3-1 | 310 | 275 |
| 3-2 | 190 | 90 |
| 3-3 | 100 | 55 |
| Comp. Ex. | | |
| 3-1 | 373 | 350 |

As shown in Table 4, the exemplary mouthwashes except example 3-1 produced much lower measurements in terms of garlic odor level, compared to the first measurement of 373 ppb as a comparative mouthwash was applied to the oral cavity. Further, the mouthwashes comprising an extract from Moutan bark still produced lower levels of garlic odor at 30 min after application. When the mouthwash (example 3-3) comprising an extract from Moutan bark in an amount of 2.0% by weight was applied, the initial garlic odor was only 100 ppb, which corresponds to about 27% of the comparative measurement, and the inhibitory effect was sustained even 30 min after application, the measurement being 55 ppb. On the other hand, when the mouthwash (comp. ex. 3-1) not comprising the active ingredient of the invention was applied, the level of volatilization of garlic odor immediately after application was 373 ppb and 30 min later, the level was 350 ppb, showing that the comparative mouthwash could not inhibit garlic odor in a lasting manner. Therefore, it was demonstrated that the mouthwash comprising an extract from Moutan bark provides long lasting and powerful eliminating and preventive effects against halitosis.

EXAMPLE 4

Preparation of Mouthwashes Comprising an Ethylacetate Fraction of the Extract From Moutan Bark The same typical ingredients as in Table 3 of Example 3 as main components were employed to prepare mouthwashes (examples 4-1 to 4-4) each of which comprises an ethylacetate fraction of the extract from Moutan bark; and a conventional mouthwash (comp. ex. 4-1).

TABLE 5

Compositions of mouthwashes (unit: weight %)

| | Ingredient | Example 4-1 | 4-2 | 4-3 | 4-4 | Comp Ex. 4-1 |
|---|---|---|---|---|---|---|
| Active ingredient | ethylacetate fraction of the extract from Moutan bark | 0.005 | 0.1 | 1 | 2 | — |
| Others | The same as in Table 3 | same | same | same | same | same |

EXPERIMENTAL EXAMPLE 4

Comparison of Inhibitory Effect of Exemplary Mouthwashes (Examples 4-1 to 4-4) With That of a Comparative Mouthwash (Comparative Example 4-1) on Volatilization of Garlic Odor in a Clinical Gargle Experiment A cross-over test was performed with 16 subjects, male or female, not having dental caries.

Commercial garlic powder which contains sulfide compounds was dispersed in water and left for 24 hours. The suspension was diluted to a solution with a value of above 700 ppb, as the concentration of sulfide compounds therein was measured using a halimeter. The diluted garlic solution was employed as a solution causing oral malodor in this experiment.

The subjects each gargled with 10 ml of the diluted garlic solution for 30 seconds, and 1 min later, levels of garlic odor were measured using a halimeter. Each of the mouthwashes (examples 4-1 to 4-4 or comparative example 4-1) was gargled in an amount of 10 ml for 30 seconds. At 30 sec, 5 min and 30 min after gargling with a mouthwash, levels of garlic odor were measured using a halimeter to determine whether inhibitory effects were sustained.

The results are shown in Table 6 below.

TABLE 6

Inhibition rates on garlic odor
{(unit: % = a measurement after gargling ÷ a measurement before gargling) × 100}

| Examples | 30 sec after gargling | 5 min after gargling | 30 min after gargling |
|---|---|---|---|
| Ex. | | | |
| 4-1 | 45.1 | 49.5 | 46.4 |
| 4-2 | 66.5 | 72.0 | 77.0 |
| 4-3 | 78.3 | 82.6 | 84.4 |
| 4-4 | 89.2 | 93.5 | 95.3 |
| Comp. Ex. | | | |
| 4-1 | 40.6 | 41.8 | 37.2 |

As shown in Table 6, the comparative mouthwash showed a slightly inhibitory effect on garlic odor for the initial 5 min after gargling, and at 30 min after gargling, however, no improvement in inhibitory effect was seen, the garlic odor being increased, indicating that the conventional mouthwash fails to provide a lasting inhibitory effect against halitosis.

On the other hand, when gargling with mouthwashes (examples) each comprising an ethylacetate fraction of the extract from Moutan bark, garlic odors were in common strongly inhibited in a concentration-dependent manner and the effects were sustained at 30 min after gargling.

EXAMPLE 5

Preparation of Toothpastes Comprising an Extract From Moutan Bark

Respective ingredients were employed as main components to prepare toothpastes (Examples 5-1 to 5-3) and conventional toothpaste (Comparative example 5-1) as listed in Table 7 below.

TABLE 7

Compositions of toothpastes (unit: weight %)

| Component | Ingredient | Ex. 5-1 | 5-2 | 5-3 | Comp. Ex. 5-1 |
|---|---|---|---|---|---|
| abrasive | calcium carbonate | 40.0 | 40.0 | 40.0 | 40.0 |
| humactant | sorbitol solution | 25.0 | 25.0 | 25.0 | 25.0 |
| frothing agent | alkyl sodium sulfate | 2.0 | 2.0 | 2.0 | 2.0 |
| binder | carboxyl methyl cellulose | 1.0 | 1.0 | 1.0 | 1.0 |
| sweetening agent | sodium saccharin | 0.2 | 0.2 | 0.2 | 0.2 |
| preservative | paraoxy benzoate ester | 0.1 | 0.1 | 0.1 | 0.1 |
| flavoring agent | combined flavorant | 1.0 | 1.0 | 1.0 | 1.0 |
| disinfectant | triclosan | 0.01 | 0.01 | 0.01 | 0.01 |
| active ingredient | extract | 0.01 | 0.5 | 2 | — |
| | purified water | balance | balance | balance | balance |

EXPERIMENTAL EXAMPLE 5

Comparison of Inhibitory Effect of Exemplary Toothpastes (Examples 5-1 to 5-3) With That of Comparative Toothpaste (Comparative Example 5-1) Against Halitosis in a Clinical Experiment A test was performed with 20 subjects, male or female, not having dental caries. 5 subjects were assigned to each.

The same meal was fed to all subjects, followed by brushing their teeth within a certain time, and 10 min later, level of halitosis was first measured using a halimeter. 30 minutes later, a second measurement was performed to determine whether inhibitory effects were sustained.

Measurement by means of a halimeter was performed in the following manner. Before a measurement, a subject breathed only through the nose with closed mouth for one minute. For measurement, the subjects had a probe inserted about 1.5 cm into the mouth, and held for about 15 seconds. At this time, the probe was not allowed to touch with the tongue. The subjects kept their lips open about 3 to 4 mm and kept breathing only through the nose.

The results are shown in Table 8 below.

TABLE 8

Inhibition rates on halitosis
{unit: % = (a measurement after brushing ÷ a measurement before brushing) × 100}

| Examples | 10 min after brushing | 30 min after brushing |
|---|---|---|
| Ex. | | |
| 5-1 | 79 | 106 |
| 5-2 | 56 | 70 |
| 5-3 | 38 | 45 |
| Comp. Ex. | | |
| 5-1 | 86 | 131 |

As shown in Table 8, the exemplary toothpastes exhibited stronger inhibitiory effects at 10 min after brushing against halitosis generated after the meal, compared to that as using the comparative toothpaste. Further, the toothpastes each comprising an extract from Moutan bark except example 5-1 still exhibited the inhibition effect at 30 min after brushing. When the toothpaste (example 5-3) comprising an extract from Moutan bark in an amount of 2.0% by weight was used, the inhibition rate was 38% and its strong effect was sustained at 30 min after brushing. On the other hand, when the toothpaste (comp. ex. 5-1) not comprising the active ingredient of the invention was used, the inhibition rate was 86% at 10 min after brushing, however, at 30 min the inhibition rate was 131%, indicating that the inhibition by the conventional toothpaste against halitosis was not sustained. Therefore, it was demonstrated that the toothpaste comprising an extract from Moutan bark is superior in terms of providing long lasting and powerful eliminating and preventive effects against halitosis, compared with the conventional toothpaste not comprising the extract.

INDUSTRIAL APPLICABILITY

As apparent from the above description, the present invention provides an oral composition effective against halitosis, comprising an extract from Moutan bark, a medicinal herb, as an active ingredient, formulated in conjunction with a conventional oral composition, thereby providing long lasting and powerful eliminating and preventive effects against halitosis.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. An oral composition effective against halitosis comprising 0.005 to 2 percent by weight, based on the total weight of the composition, of an ethylacetate fraction of an extract from Moutan bark as an active ingredient, wherein the ethylacetate fraction is obtained by suspending the extract in water and then solvent fractionating the suspension with n-hexane, dichloromethane, and ethylacetate in sequential order.

2. An oral composition effective against halitosis comprising 0.005 to 2 percent by weight, based on the total weight of the composition, of an ethylacetate fraction of an extract from Moutan bark as an active ingredient, wherein the ethylacetate fraction is obtained by extracting Moutan bark with n-hexane and then extracting the residual Moutan bark with ethylacetate.

3. The oral composition as set forth in claim 1, wherein the ethylacetate fraction is present in an amount of 0.01 to 2 percent by weight.

4. The oral composition as set forth in claim 2, wherein the ethylacetate fraction is present in an amount of 0.01 to 2 percent by weight.

* * * * *